(12) United States Patent
Luettke et al.

(10) Patent No.: US 6,455,700 B1
(45) Date of Patent: Sep. 24, 2002

(54) PROCESS FOR PREPARING GUANIDINE AND AMIDINE DERIVATIVES

(75) Inventors: Sven Luettke; Andreas Mathes, both of Ockenheim (DE)

(73) Assignee: Boehringer Ingelheim Pharma KG., Ingelheim (DE)

( * ) Notice: Subject to any disclaimer, the term of this patent is extended or adjusted under 35 U.S.C. 154(b) by 0 days.

(21) Appl. No.: 10/085,592

(22) Filed: Feb. 27, 2002

Related U.S. Application Data

(62) Division of application No. 09/897,664, filed on Jul. 2, 2001, now Pat. No. 6,103,719.

(30) Foreign Application Priority Data

May 30, 1998 (DE) ......................... 198 24 470

(51) Int. Cl.$^7$ ............................. C07D 211/06
(52) U.S. Cl. ............................................... 546/223
(58) Field of Search ................................. 546/223

(56) References Cited

U.S. PATENT DOCUMENTS 5,364,943 A * 11/1994 Rosen et al. ............... 546/223
5,710,155 A * 1/1998 Schnorrenberg et al. .... 514/255
6,294,556 B1 * 9/2001 Schnorrenberg ............ 514/331

* cited by examiner

*Primary Examiner*—Joseph K. McKane
*Assistant Examiner*—Golam M. M. Shameem
(74) *Attorney, Agent, or Firm*—Robert P. Raymond; Anthony P. Bottino; Alan R. Stempel

(57) ABSTRACT

The invention relates to new compounds of general formula I

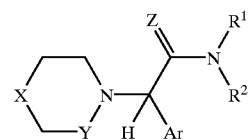

or the pharmaceutically acceptable salts thereof, wherein
X=N—$R^3$ or CH—$R^4$,
Y=$CH_2$ or $(CH_2)_2$,
Z=O or $H_2$;
and $R^1$, $R^2$, $R^3$, $R^4$ and Ar have the meanings given in the specification, and the preparation and use thereof. The new compounds are valuable neurokinin (tachykinin) antagonists.

3 Claims, No Drawings

PROCESS FOR PREPARING GUANIDINE AND AMIDINE DERIVATIVES

APPLICATION DATA

This application is a divisional of U.S. Ser. No. 09/897,664 Jul. 2, 2001 which is a divisional of U.S. Pat. No. 6,103,719.

The invention relates to new guanidine and amidine derivatives of general formula I and the pharmaceutically acceptable salts thereof, processes for preparing them and pharmaceutical compositions containing these compounds. The compounds are valuable neurokinin (tachykinin) antagonists.

The abbreviations used in this specification and claims are explained as follows:

Boc=t-butyloxycarbonyl
DC=thin layer chromatogram
DMF=dimethylformamide
EE=ethyl acetate
FAB-MS=fast atom bombardment mass spectroscopy
RT=room temperature
TBTU=O-benzotriazolyl-tetramethyluronium tetrafluoroborate
TEA=triethylamine
THF=tetrahydrofuran A simplified format is used for the formulae. In the representations of compounds, all $CH_3$ substituents are indicated by a hyphen, e.g.

denotes

The invention relates to new guanidine and amidine derivatives of general formula I or the pharmaceutically acceptable salts thereof, wherein
X denotes N—$R^3$ or CH—$R^4$, wherein $R^3$ denotes $R^3$ wherein $R^5$, $R^6$ and $R^7$ independently of one another denote H, alkyl, cycloalkyl, alkenyl, aryl, aralkyl, alkanoyl, benzoyl, heteroaryl, dialkylamino, dialkylaminoalkyl, trialkylammoniumalkyl, cyano, alkyloxycarbonyl, aralkyloxycarbonyl, OH, O-alkyl or O-aryl, wherein the alkyl groups contain 1 to 5 carbon atoms, the cycloalkyl groups contain 3 to 6 carbon atoms, the alkenyl groups contain 2 to 5 carbon atoms, aryl denotes phenyl, or phenyl or naphthyl substituted by methyl or halogen (F, Cl, Br, I);

or $R^5$ and $R^6$ or $R^6$ and $R^7$ together form the group $(CH_2)_2$—, —$(CH_2)_3$—, —$(CH_2)_4$—, —$(CH_2)_5$— or —$(CH_2)_2$ $O(CH_2)_2$;

or $R^3$ denotes and $R^4$ denotes wherein $R^5$ to $R^7$ are as hereinbefore defined and
$R^8$=H, alkyl with 1 to 5 carbon atoms or cycloalkyl with 3 to 6 carbon atoms or
$R^7$+$R^8$ together form the group —$(CH_2)_2$—, —$(CH_2)_3$—, —$(CH_2)_4$—, —$(CH_2)_5$— or —$(CH_2)_2O(CH_2)_2$—;
or $R^4$ denotes wherein $R^5$ is as hereinbefore defined;
Y denotes $CH_2$ or $(CH_2)_2$;
Z denotes O or $H_2$;
Ar denotes unsubstituted or mono- to 5-substituted phenyl, or unsubstituted or mono- or disubstituted naphthyl [wherein the substituents of the phenyl and naphthyl independently of one another denote halogen (F, Cl, Br, I), OH, $(C_{1-4})$alkyl, O—$(C_{1-4})$alkyl, $CF_3$, OCF$_3$ or NR$^9$R$^{10}$ (wherein R$^9$ and R$^{10}$ independently of one another denote H, methyl or acetyl)] or Ar is phenyl substituted by —OCH$_2$O— or —O(CH$_2$)$_2$O—;

R$^1$ denotes phenyl(C$_{1-4}$)alkyl or phenyl(C$_{1-4}$)alkanoyl or naphthyl(C$_{1-4}$)alkyl or naphthylacetyl, wherein phenyl may be substituted by 1 to 3 substituents, wherein the substituents independently of one another denote halogen (F, Cl, Br, I), (C$_{1-4}$)alkyl, O—(C$_{1-4}$)alkyl, CF$_3$, OCF$_3$ or NR$^{19}$R$^{20}$ (wherein R$^{19}$ and R$^{20}$ independently of one another denote H, methyl or acetyl); and R$^2$ denotes H, (C$_{1-4}$)alkyl, (C$_{3-6}$)cycloalkyl, CH$_2$COOH, —CH$_2$C(O)NH$_2$, OH or phenyl(C$_{1-4}$)alkyl.

The compounds according to the invention are valuable neurokinin (tachykinin) antagonists which have both substance P antagonism and also neurokinin-A- or neurokinin-B-antagonistic properties. They are useful for the treatment and prevention of neurokinin-mediated diseases.

Compounds of general formula I may contain acid groups, mainly carboxyl groups, and/or basic groups such as amino functions, for example. Compounds of general formula I may therefore occur as internal salts, salts with pharmaceutically acceptable inorganic acids such as hydrochloric acid, sulphuric acid, phosphoric acid, sulphonic acid or organic acids (such as, for example, maleic acid, fumaric acid, citric acid, tartaric acid or acetic acid) or as salts with pharmaceutically acceptable bases such as alkali metal or alkaline earth metal hydroxides or carbonates, zinc or ammonium hydroxides or organic amines such as e.g. diethylamine, triethylamine, triethanolamine, etc.

The compounds according to the invention may occur as racemates, but may also be obtained as pure enantiomers, i.e. in the (R) or (S) form. Compounds which occur as racemates or in the (S) form are preferred.

Results of investigations into the compound according to the invention: The receptor affinity for the NK$_1$ receptor (substance P receptor) is determined on human lymphoblastoma cells (IM-9) with cloned NK$_1$ receptors, by measuring the displacement of $^{125}$I-labelled substance P. The K$_i$ values thus obtained show the efficacy of the compounds.

| Example no. | K$_i$ [nMol/L] |
| --- | --- |
| 1 | 0.45 |
| 2 | 0.30 |
| 3 | 0.20 |
| 4 | 0.53 |
| 5 | 6.28 |
| 6 | 0.88 |
| 7 | 1.45 |
| 8 | 0.19 |
| 9 | 0.14 |
| 10 | 0.12 |
| 12 | 0.32 |
| 27 | 1.11 |
| 28 | 4.16 |
| 29 | 0.87 |
| 30 | 0.17 |
| 31 | 8.96 |
| 32 | 0.20 |
| 33 | 13.25 |
| 34 | 0.37 |
| 35 | 0.78 |

The compounds according to the invention are valuable neurokinin (tachykinin) antagonists which have both substance P antagonism and also neurokinin-A- or neurokinin-B-antagonistic properties. They are useful for the treatment and prevention of neurokinin-mediated diseases:

For preventing or treating inflammatory or allergic diseases of the respiratory tract such as asthma, chronic bronchitis, hyperreactive respiratory tract, emphysema, rhinitis, cough, of the eyes, such as conjunctivitis and iritis, of the skin, such as dermatitis in contact eczema, urticaria, psoriasis, sunburn, insect bites, itching, sensitive or hypersensitive skin, of the gastro-intestinal tract such as gastric and duodenal ulcers, ulcerative colitis, Crohn's disease, irritable bowel, Hirschsprung's disease, of the joints, such as rheumatoid arthritis, reactive arthritis and Reiter syndrome; for treating diseases of the central nervous system, such as dementia, Alzheimer's disease, schizophrenia, psychoses, depression, headache (e.g. migraine or tension headaches), epilepsy; Parkinson's disease, stroke, for treating Herpes zoster and postherpetic pain, tumours, collagenoses, dysfunction of the urinary tract, haemorrhoids, nausea and vomiting, triggered by radiation or cytostatic therapy, for example, or movement and pain of all kinds.

The invention therefore also relates to the use of the compounds according to the invention as curative agents and pharmaceutical preparations which contain these compounds. They are preferably used in humans. The compounds according to the invention may be administered by intravenous, subcutaneous, intramuscular, intraperitoneal or intranasal route, by inhalation, by transdermal route, if desired with the aid of iontophoresis or enhancers known from the literature, and by oral route.

For parenteral administration the compounds of formula I or the physiologically acceptable salts thereof are brought into solution, suspension or emulsion, optionally with the substances conventionally used for this, such as solubilisers, emulsifiers or other adjuvants. Suitable solvents include, for example: water, physiological saline solutions or alcohols, e.g. ethanol, propandiol or glycerol, sugar solutions such as glucose or mannitol solutions or a mixture of different solvents.

Moreover, the compounds may be administered by means of implants, e.g. of polylactide, polyglycolide or polyhydroxybutyric acid or intranasal preparations. Preferred compounds of general formula 1 are those wherein X denotes N—R$^3$ or CH—R$^4$, wherein R$^3$ denotes

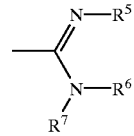

wherein R$^5$, R$^6$ and R$^7$ independently of one another denote H, alkyl, cycloalkyl, aryl, aralkyl, alkanoyl, benzoyl, dialkylamino, dialkylaminoalkyl, trialkylammoniumalkyl, cyano, alkyloxycarbonyl, aralkyloxycarbonyl, OH, O-alkyl or O-aryl, wherein the alkyl groups contain 1 to 4 carbon atoms, the cycloalkyl groups contain 3 to 6 carbon atoms, aryl denotes phenyl or phenyl substituted by methyl or halogen (F, Cl, Br, I);

or R$^5$ and R$^6$ or R$^6$ and R$^7$ together form the group —(CH$_2$)$_2$—, —(CH$_2$)$_3$—, —(CH$_2$)$_4$—, —(CH$_2$)$_5$— or —(CH$_2$)$_2$ O(CH$_2$)$_2$;

or R³ is

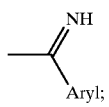

and R⁴ is

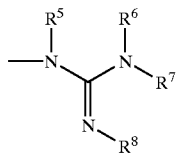

wherein R⁵ to R⁷ are as hereinbefore defined and
R⁸=H, alkyl with 1 to 5 carbon atoms or cycloalkyl with 3 to 6 carbon atoms or
R⁷+R⁸ together form the group —(CH₂)₂—, —(CH₂)₃—, —(CH₂)₄—, —(CH₂)₅— or —(CH₂)₂ O(CH₂)₂—;
Y denotes CH₂ or (CH₂)₂;
Z denotes O or H₂;
Ar denotes unsubstituted or mono- to 5-substituted phenyl [wherein the substituents of the phenyl independently of one another denote halogen (F, Cl, Br, I), OH, (C₁-C)alkyl, O—(C₁₋₄)alkyl, CF₃, OCF₃ or NR⁹R¹⁰ (wherein R⁹ and R¹⁰ independently of one another denote H, methyl or acetyl)] or Ar is phenyl substituted by —OCH₂O— or —O(CH₂)₂O—;
R¹ denotes phenyl(C₁–C₄)alkyl or phenyl(C₁–C₄) alkanoyl, wherein phenyl may be substituted by 1 to 3 substituents, wherein the substituents independently of one another denote halogen (F, Cl, Br, I), (C₁₋₄)alkyl, O—(C₁₋₄)alkyl, CF₃, OCF₃ or NR¹⁹R²⁰ (wherein R¹⁹ and R²⁰ independently of one another denote H, methyl or acetyl); and
R² denotes H, (C₁₋₄)alkyl or (C₃₋₆)cycloalkyl.
Particularly preferred are those compounds wherein
X denotes N—R³ or CH—R⁴, wherein
R³ denotes

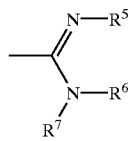

and R⁴ denotes

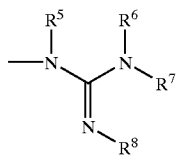

and R⁵ to R⁸, Z, Ar, R¹ and R² are as hereinbefore defined, and Y denotes CH₂.
Of these compounds, the preferred ones are those wherein Z is oxo, and/or Ar is unsubstituted phenyl, particularly those wherein Ar is phenyl mono- or disubstituted by halogen, preferably Ar is dichlorophenyl; and/or wherein R¹ denotes substituted phenylacetyl (preferably 3,4-di-trifluoromethylphenyl-acetyl) or wherein R¹ is substituted phenylethyl, wherein the phenyl is substituted by 2 substituents which, independently of one another, denote halogen (F, Cl, Br, I), (C₁₋₄)alkyl or CF₃, particularly wherein the substituents of the phenyl are CF3 CH₃ or F, (preferably wherein the two substituents of the phenyl are CF₃); and/or wherein R² is (C₁₋₄)alkyl, preferably wherein R² is methyl.

Compounds of formula I are preferred wherein the group

is

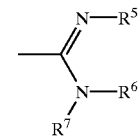

One aspect of the invention relates to compounds of formula I wherein X denotes the group CR⁴, wherein
R⁴ is

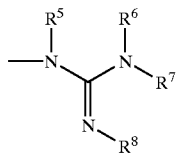

wherein
R⁵, R⁶, R⁷ and R⁸ independently of one another denote H, alkyl with 1 to 4 carbon atoms or cycloalkyl with 3 to 6 carbon atoms; or
R⁷ and R⁸ together form the group (CH₂)₂, (CH₂)₃, (CH₂)₄ or (CH₂)₅. Compounds wherein R⁵ and R⁶ denote H and R⁷ and R⁸ together form the group (CH₂)₂ or those wherein R⁵ and R⁶ denote H and R⁷ and R⁸ are cyclohexyl are preferred.

Another important aspect of the invention relates to compounds of formula I wherein X is the group NR³ wherein
R³ is

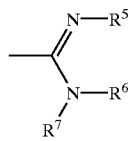

wherein
R⁵ and R⁶ independently of one another denote H, alkyl with 1 to 4 carbon atoms, cycloalkyl with 3 to 6 carbon atoms, phenyl, or phenyl, benzyl or benzoyl substituted by methyl or halogen (F, Cl, Br, I), CN, alkyloxycarbonyl (wherein the alkyl group contains 1 to 4 carbon atoms), benzyloxycarbonyl, alkoxy with 1 to 4 carbon atoms or dialkylamine (wherein the alkyl groups contain 1 to 4 carbon atoms),
R⁷ denotes H or alkyl with 1 to 4 carbon atoms; or R⁵ and R⁶ or R⁶ and R⁷ together form the group (CH₂)₂, (CH₂)₃, (CH₂)₄ or (CH₂)₅; or R⁶ and R⁷ together form the group —(CH)₂—O—(CH₂)₂—.
Of these compounds, the preferred ones are those wherein
a) R⁵ and R⁶ independently of one another denote H, alkyl with 1 to 4 carbon atoms, cycloalkyl with 3 to 6 carbon atoms, phenyl, phenyl, benzyl or benzoyl substituted by methyl or halogen (F, Cl, Br, I);

$R^7$ is H or alkyl with 1 to 4 carbon atoms or $R^5$ and $R^6$ or $R^6$ and $R^7$ together form the group $(CH_2)_2$, $(CH_2)_3$, $(CH_2)_4$ or $(CH_2)_5$; or $R^6$ and $R^7$ together form the group —$(CH_2)_2$—O—$(CH_2)_2$—;

b) $R^5$ and $R^6$ independently of one another denote H, alkyl with 1 to 4 carbon atoms, cyclohexyl, phenyl, methyl-substituted phenyl, benzyl or benzoyl;

$R^7$ is H or methyl; or $R^5$ and $R^6$ together form the group $(CH_2)_2$ or $R^6$ and $R^7$ together form the group $(CH_2)_5$ or —$(CH)_2$—O—$(CH_2)_2$—;

c) $R^5$-denotes H, alkyl with 1 to 4 carbon atoms, cyclohexyl, methyl-substituted phenyl, benzyl or benzoyl;

$R^6$ denotes H, alkyl with 1 to 3 carbon atoms, cyclohexyl, phenyl, methyl-substituted phenyl or benzyl;

$R^7$ is H or methyl; or $R^5$ and $R^6$ together form the group —$(CH_2)_2$— or $R^6$ and $R^7$ together form the group $(CH_2)_2$—O—$(CH_2)_2$—;

d) $R^5$ and $R^6$ independently of one another denote H, $CH_3$, $CH(CH_3)_2$, phenyl or benzyl, $R^7$ is H or $CH_3$, or $R^5$ and $R^6$ together form the group —$CH_2CH_2$— or $R^6$ and $R^7$ together form the group —$(CH_2)_2$—O—$(CH_2)_2$—.

Particularly preferred are compounds of general formula I, wherein X denotes the group

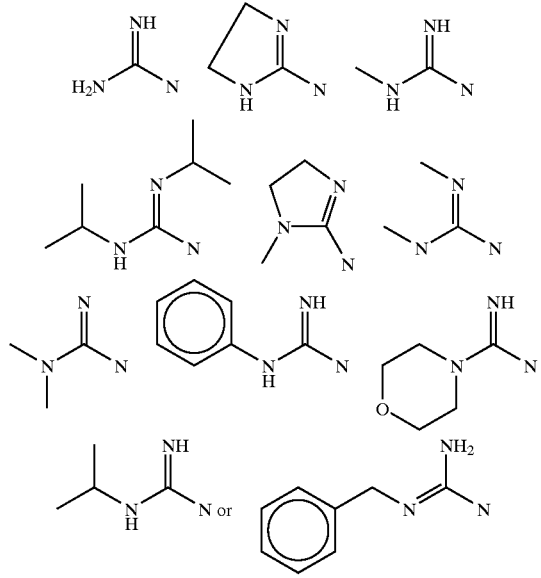

The following compounds are particularly preferred:

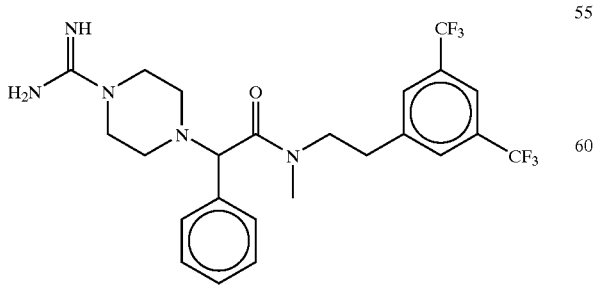

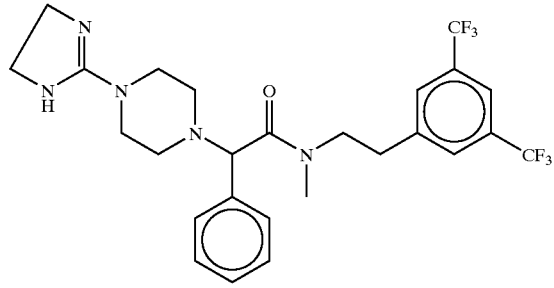

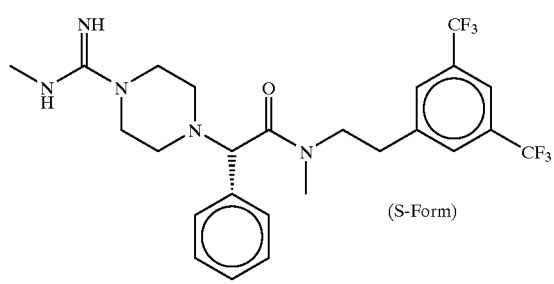

(S-Form)

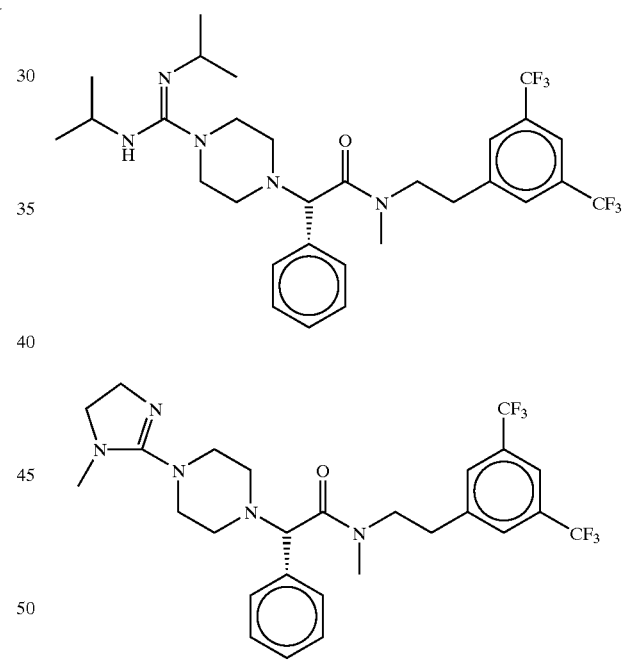

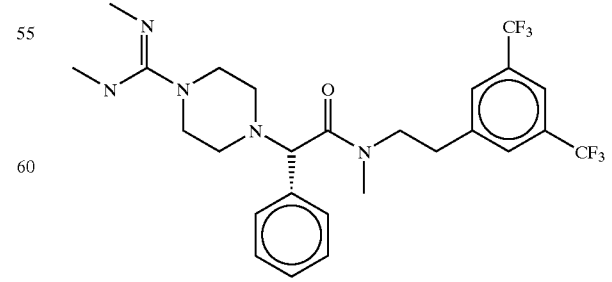

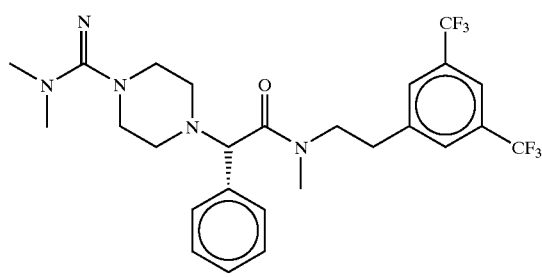

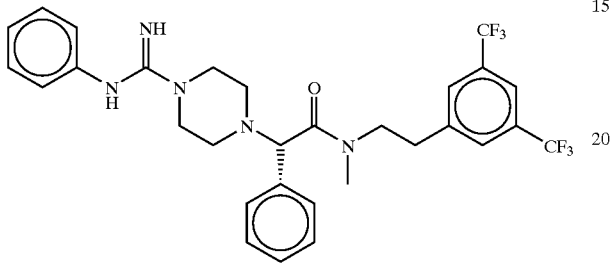

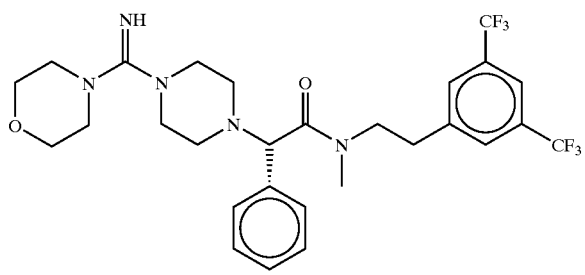

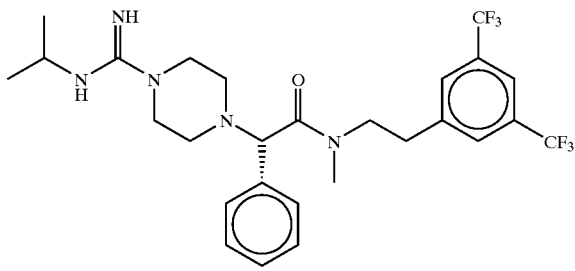

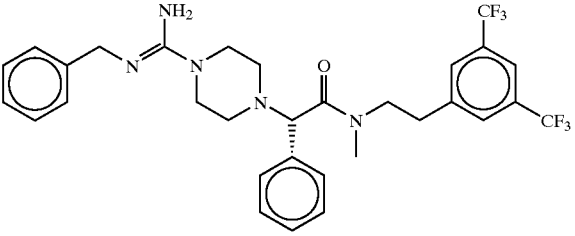

The compounds may be prepared by methods known per se. Advantageous methods are shown and described in the diagrams which follow.

The compounds of general formula

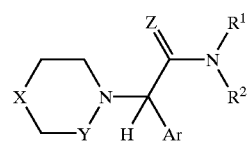

I wherein

X denotes N—R³, wherein R³ is

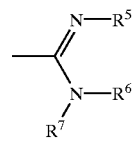

may be prepared by reacting a compound of general formula I wherein R³ denotes hydrogen with the corresponding amino-iminomethanesulphonic acid, the corresponding carbodiimide or thiourea. This process is illustrated by methods A to C for pounds wherein Y is CH₂, Ar is phenyl, Z is oxo, R¹ is difluorophenylethyl and R² is methyl. However, the process can be used analogously for all compounds of formula I wherein X is NR³.

Diagram 1 (Method A)

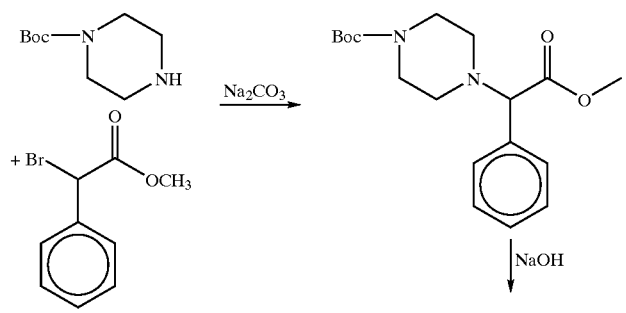

-continued

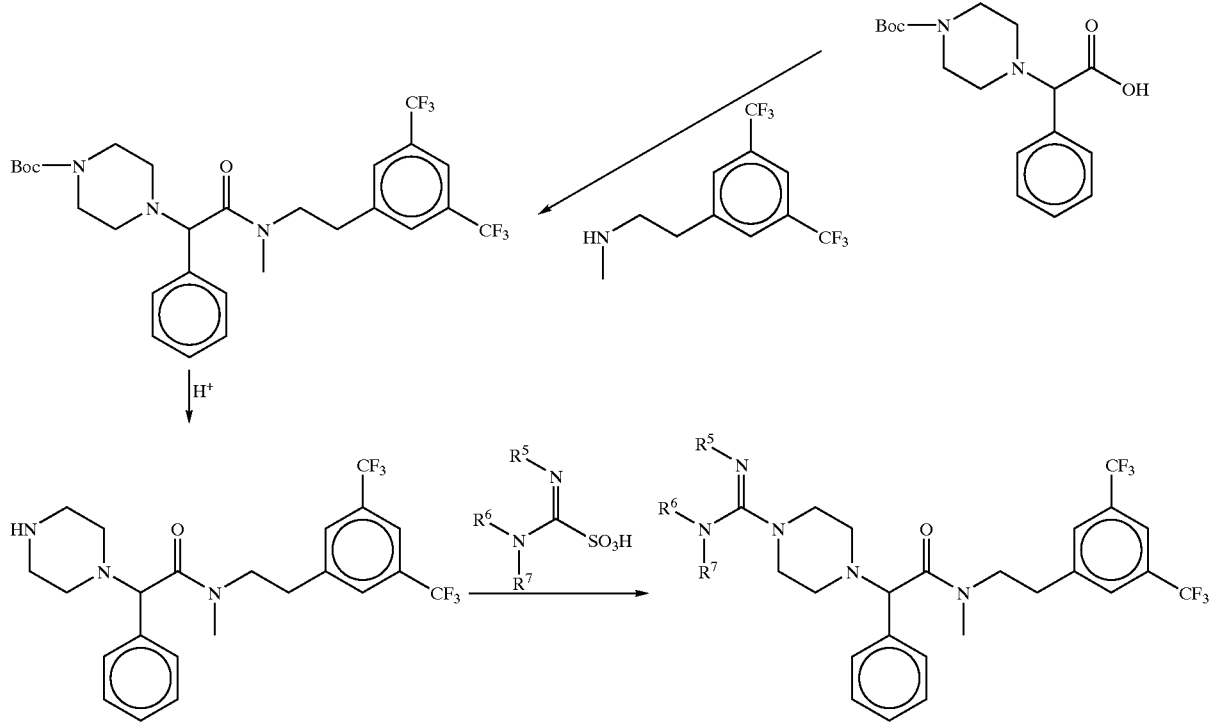

Method A

Piperazine having a protecting group in the 1 position is reacted with 2-halophenyl-acetate to obtain N-protected piperazinyl-phenylacetate. This is saponified under suitable conditions, e.g. with sodium hydroxide solution, to obtain the corresponding carboxylic acid. This is then linked to an amine according to the invention, e.g. N-methyl-3,5-bis-trifluoromethylphenethyl-amine, using a suitable coupling reagent such as TBTU. In the next step the protecting group is cleaved from the piperazine part of the molecule using a suitable cleaving reagent. In the last step of the reaction, the free piperazine-N is reacted with unsubstituted or substituted amino-iminomethanesulphonic acid (which is obtained for example by oxidation of the corresponding thiourea using $H_2O_2$) to obtain the desired guanidine. Compounds of the type in Examples 1–3 may advantageously be prepared by method A, for example.

Diagram 2 (Method B)

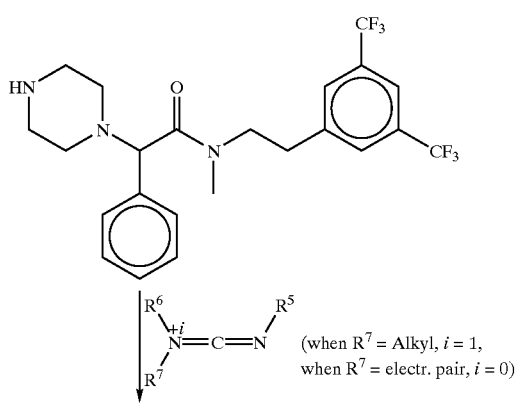

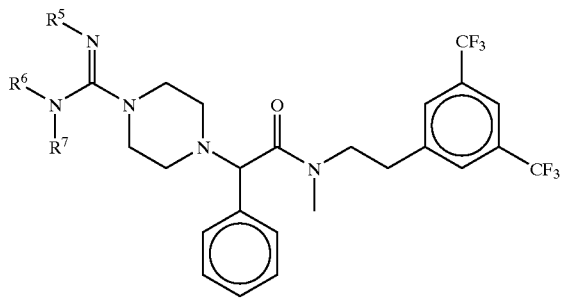

Method B

The same procedure is used as in method A, except that in the last step, the reaction is carried out with carbodiimides instead of the substituted methanesulphonic acid. These may be either N,N'-disubstituted carbodiimides or N,N,N'-trisubstituted carbodiimides, which are then used in the form of a salt, e.g. the iodide.

The compounds of the type in Examples 4 to 7 may advantageously be prepared according to method B, for example.

Diagram 3 (Method C)

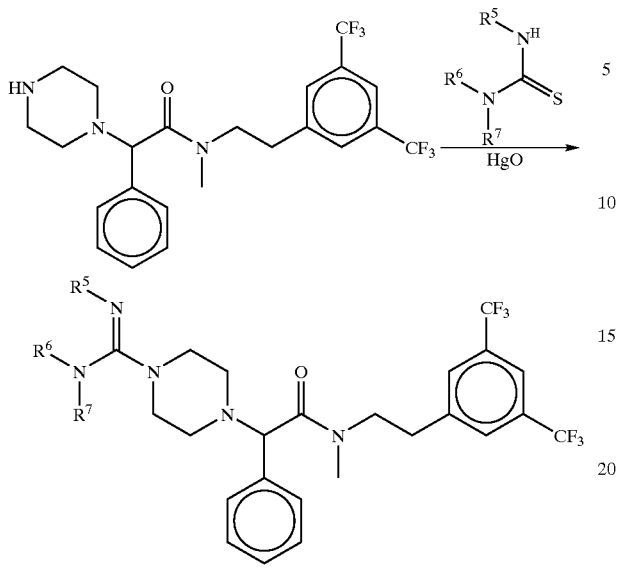

Method C

The same procedure is used as in method A, except that in the last step, instead of the substituted methanesulphonic acid, a substituted thiourea is reacted together with $H_gO$.

Compounds of the type in Example 9 may advantageously be prepared according to method C, for example.

The compound of general formula

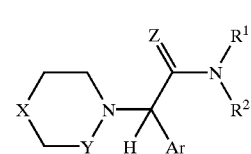

I may also be prepared by reacting the corresponding piperazine derivative or piperidine derivative with the corresponding amide. This process is illustrated by method D and analogous method E for compounds wherein Y denotes $CH_2$, Ar is phenyl, Z is oxo, $R^1$ is difluorophenylethyl and $R^2$ is methyl. The process may be used analogously, however, for all compounds of formula I wherein X is $NR^3$ or $CR^4$. Particularly preferred are compounds wherein
   $R^3$ denotes

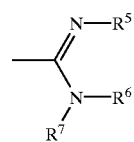

or
   $R^4$ denotes

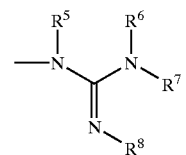

The reaction is carried out in an inert solvent in the presence of a base.
Diagram 4 (Method D)

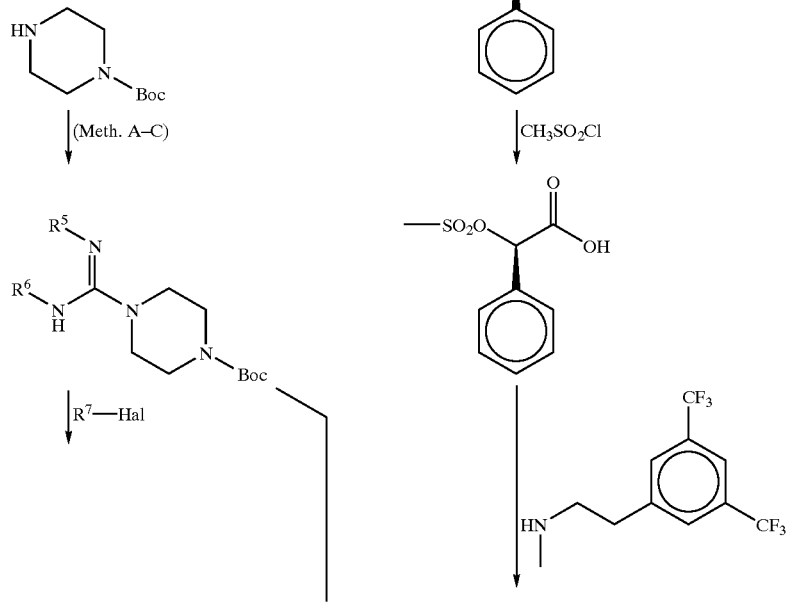

-continued

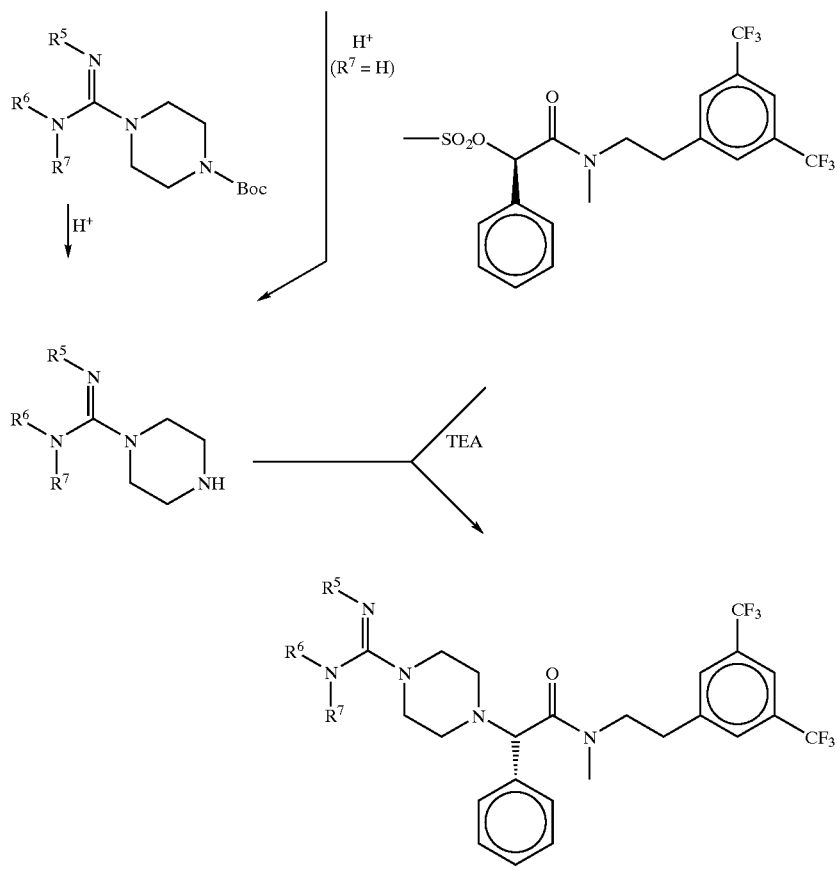

Method D

Analogously to the last step in method A, first of all, piperazine protected in the 1 position is reacted with unsubstituted or substituted amino-iminomethanesulphonic acid. Other substituents may be introduced into the resulting guanidine by alkylation or acylation if required. In the next step the piperazine derivative is obtained with an unsubstituted piperazine-N by cleaving the protecting group with a cleaving reagent.

The reactant for this piperazine derivative is obtained as shown on the right in Diagram 4. (R)-Mandelic acid is reacted with methanesulphonic acid halide to obtain the (R)-2-(methanesulphonyloxy)-acetic acid. This is then reacted with a coupling reagent and the correspondingly substituted phenethylamine to form the corresponding amide, or it is converted into the corresponding acid halide (e.g. with $SOCl_2/SO_2Cl_2$) and then converted, with the suitably substituted phenethylamine, into the corresponding amide. In the last step the amide thus obtained is reacted with the piperazine derivative described above, whereupon a C—N bond is formed, with elimination of methanesulphonate, whilst at the same time the chiral centre is reversed. The reaction is carried out in an inert solvent such as e.g. DMF or acetonitrile in the presence of a base such as TEA or N-methylmorpholine, for example, at temperatures between 20° C. and 120° C. The reaction time is between 0.5 h and 48 h.

Compounds of the type in Example 8 may advantageously be synthesised according to method D.

Scheme 5 (Method E)

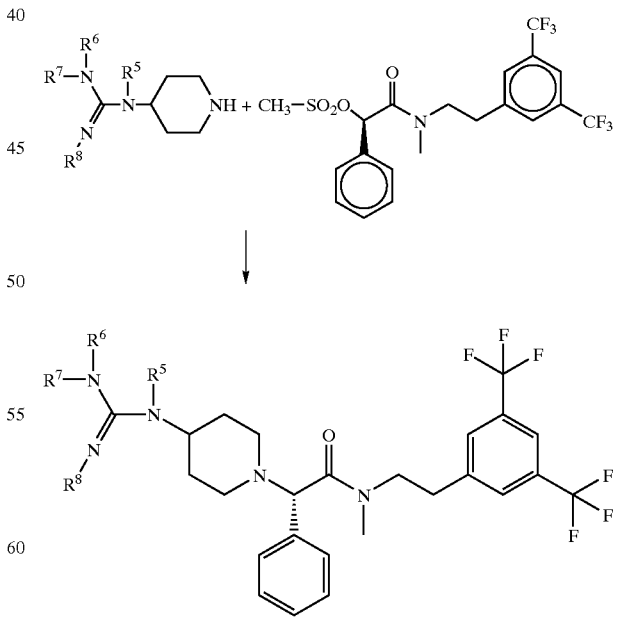

The method is carried out analogously to method D. Compounds of the type in Example 36 may advantageously be synthesised according to Method E.

EXAMPLES

Example 1

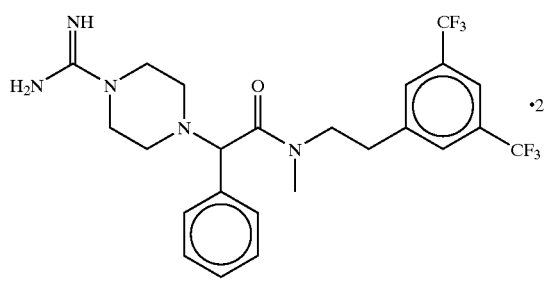

(R,S)-1-Amidino-4-[2-phenylacetic acid-N-methyl-N-(3,5-bis-trifluoromethyl-phenyl-ethyl)-amide]-piperazine, dihydrochloride 1.09 g of (R,S)-1-[2-phenylacetic acid-N-methyl-N-(3,5-bis-trifluoromethyl-phenylethyl)-amide]-piperazine (2 mmol) were mixed with 5 ml of water, 5 ml of methanol, 1.1 g of $K_2CO_3$ (8 mmol) and 0.5 g of aminoiminomethanesulphonic acid (4 mmol) and stirred for 2 days at RT. The reaction mixture was diluted with water and extracted several times with EE and ether. The organic phases were combined, dried with $MgSO_4$ and evaporated to dryness. The solid residue was chromatographed over silica gel and the fractions found to be uniform by DC were combined and evaporated to dryness. The residue was dissolved in methanol, mixed with ethereal HCl, evaporated to dryness, stirred with ether, suction filtered and dried. 80 mg of the compound of Example 1 are obtained (yield 7%).

melting point: 128–138° C.

FAB-MS: $(M+H)^+=516.4$.

Examples 2 and 3 were prepared analogously:

Example 2

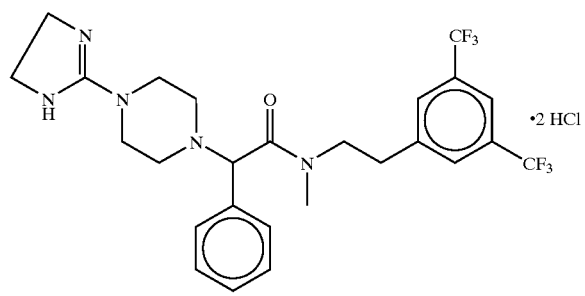

melting point: 163–173° C.

FAB-MS: $(M+H)^+=542.2$.

Example 3

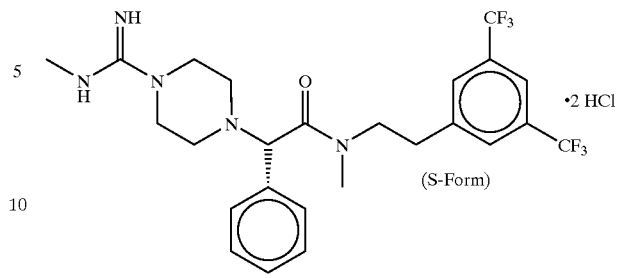

melting point: 69–79° C.
FAB-MS: $(M+H)+=530.2$.

Example 4

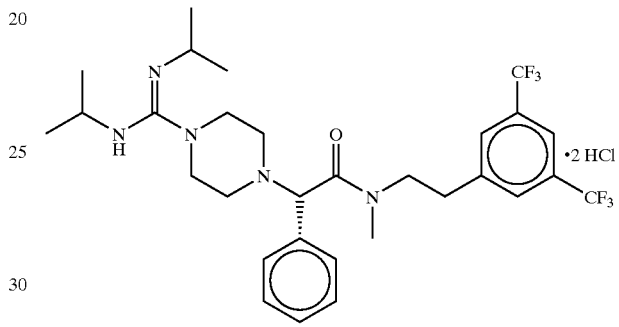

0.82 g of (R,S)-1-[2-phenylacetic acid-N-methyl-N-(3,5-bis-trifluoromethyl-phenylethyl)-amide]-piperazine were mixed with 20 ml of $CH_2Cl_2$, 0.5 ml of TEA and 0.215 g of N,N'-diisopropylcarbodiimide and the reaction mixture was stirred for 4 days at RT. It was then evaporated to dryness and the residue was chromatographed over silica gel. The fractions found to be uniform by DC were combined and concentrated by evaporation, the residue was taken up in methanol, mixed with ethereal HCl and again evaporated to dryness. The solid residue was stirred with ether, suction filtered and dried, to obtain 0.35 g of the compound of Example 4 as a racemate (yield 35%)

melting point: 176–186° C. (decomp.)
FAB-MS: $(M+H)^+=600.6$.

Examples 5 to 7 were prepared analogously to Example 4.

Example 5

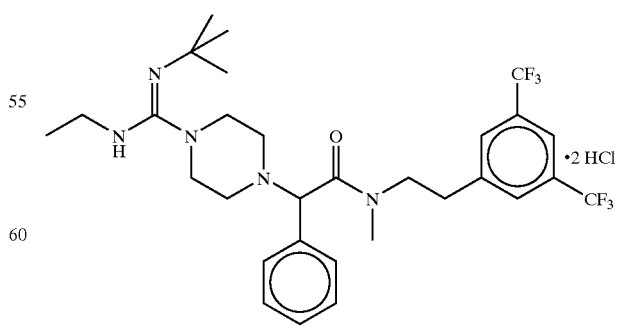

melting point: 174–184° C. (decomp.)
FAB-MS: $(M+H)^+=600.6$.

Example 6

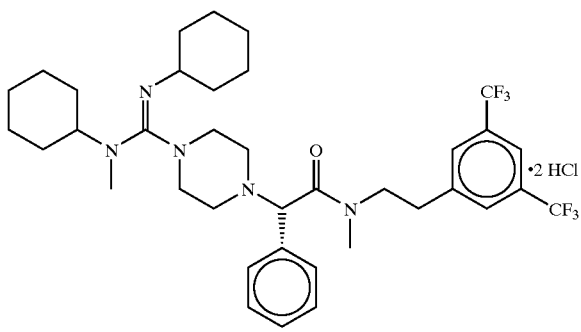

melting point: 145–158° C.
$[\alpha]_D^{20} = 24.8°$ (DMSO)

Example 7

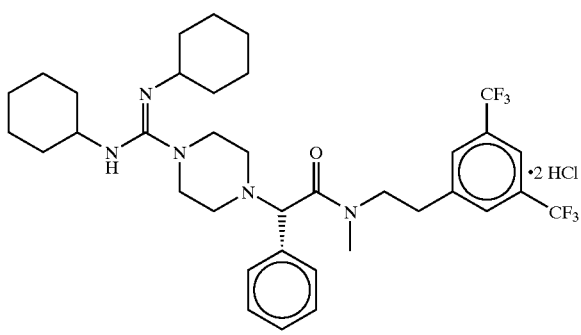

melting point: 182–188° C. (decomp.)
FAB-MS: (M+H)⁺=680.3.

Example 8

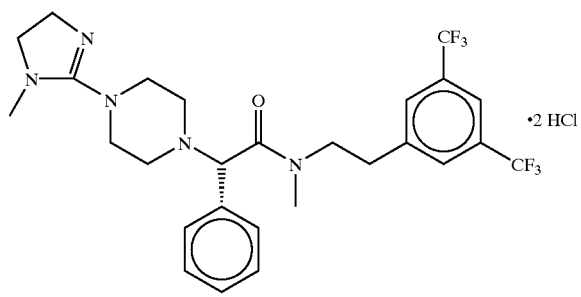

Preparation of 1-(1-methyl-imidazolin-2-yl)-piperazine 1.86 of Boc-piperazine were combined with 25 ml of water, 25 ml of methanol, 2.77 g of K₂CO₃ and 1.5 g of imidazoline-2-sulphonic acid and stirred for 2 days at RT. After dilution with water the mixture was extracted with EE and chromatographed over silica gel. 0.8 g of 1-(imidazolin-2-yl)-4-Boc-piperazine were obtained. This substance was combined with 6.2 ml of DMF and 136 mg of NaH dispersion (60%). After one hour, 0.214 ml of methyl iodide was added dropwise and the reaction mixture was left for three days at RT. It was combined with water, extracted with EE and chromatographed over silica gel. In this way, 0.47 g of 1-(1-methylimidazolin-2-yl)-4-Boc-piperazine was obtained, which was treated with 5 ml of 4N HCl in dioxane at RT. After one hour, the mixture was concentrated by evaporation, stirred with ether and evaporated to dryness in vacuo. 0.38 g of 1-(1-methyl-imidazolin-2-yl)-piperazine dihydrochloride was thus obtained as a solid substance (yield 15%)

0.73 g of (R)-mandelic acid-o-methanesulphonate-N-methyl-N-(3,5-bistrifluoromethylphenylethyl)-amide was combined with 15 ml of DMF, 0.7 ml of TEA and 0.38 g of 1-(1-methyl-imidazolin-2-yl)-piperazine dihydrochloride and stirred for 3 h at 65° C. The reaction mixture was evaporated down, the residue was first treated with NaHCO₃ solution and then extracted twice with EE. The organic phases were combined, concentrated by evaporation under reduced pressure and the residue was chromatographed over silica gel. The product thus obtained was dissolved in ether, washed with NaHCO₃, and evaporated to dryness with MgSO₄.

The residue was dissolved in methanol, mixed with excess ethereal HCl and evaporated to dryness, to obtain 0.18 g of the compound of Example 8 (yield 19%)

melting point: 115–125° C.

FAB-MS: (M+H)⁺=556.9.

Example 9

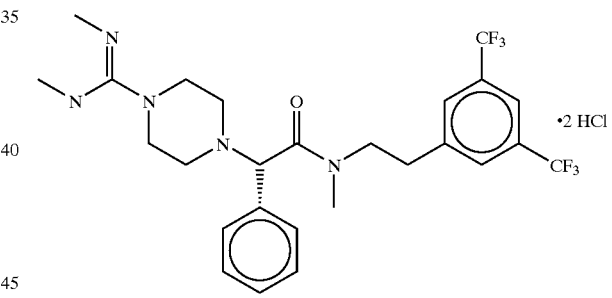

0.31 g of N,N'-dimethylthiourea, 26 ml of CH₂Cl₂, 0.63 g of Na₂SO₄, 1.25 g of HgO, 0.77 g of (S)-1-[2-phenylacetic acid-N-methyl-N-(3,5-bistrifluoromethyl-phenylethyl)-amide]-piperazine and 0.42 ml of TEA were combined, stirred for 3 days at RT and then refluxed for 4 hours. The reaction mixture was concentrated by evaporation under reduced pressure and the residue was treated with water and EE. The organic phase separated off was filtered and evaporated to dryness. The residue was chromatographed over silica gel. The eluate obtained was evaporated down, dissolved in methanol, mixed with ethereal HCl, evaporated to dryness once more, the residue was washed with ether and dried. 0.15 g of the compound of Example 9 was obtained as a white solid (yield 16%)

melting point: 126–140° C.

FAB-MS: (M+H)⁺=543.8.

Example 10
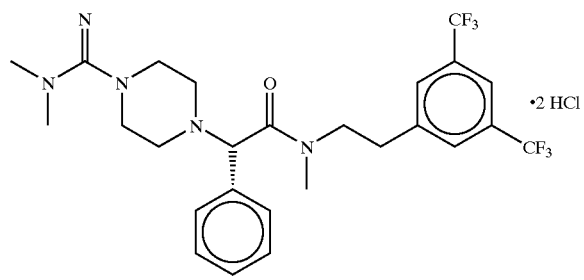
melting point: 131–141° C.
$[\alpha]_D^{20} = 20.6°$ (DMSO)
The Examples which follow may be prepared using the methods described.
Example 11
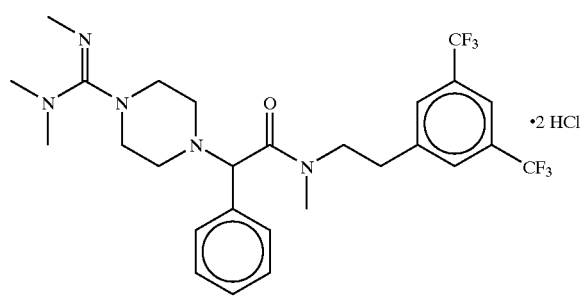
(+)-enantiomer melting point: 171–181° C.
$[\alpha]20/D = 28.4°$ (DMSO)
Example 12
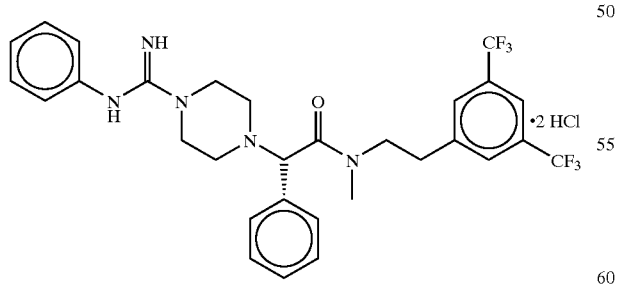
melting point: 240–245° C. (decomp.)
FAB-MS: (M+H)⁺=592.1.
Example 13
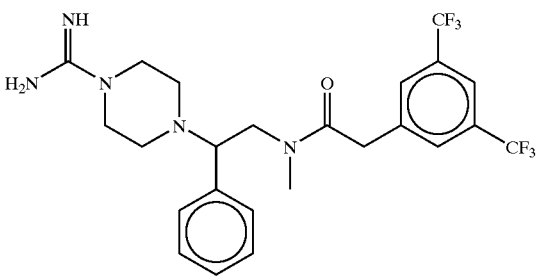
Example 14
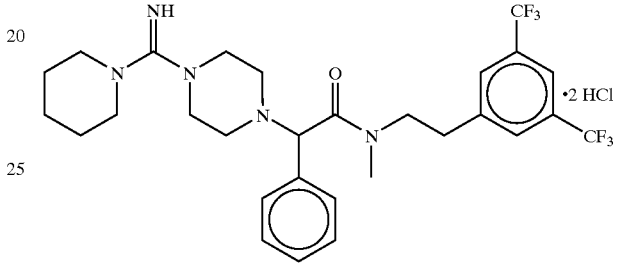
(+)-enantiomer FAB-MS: (M+H)⁺=584.
Example 15
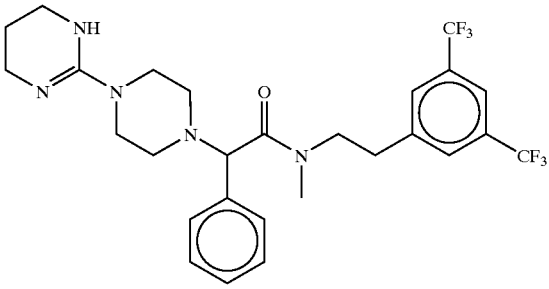
Example 16
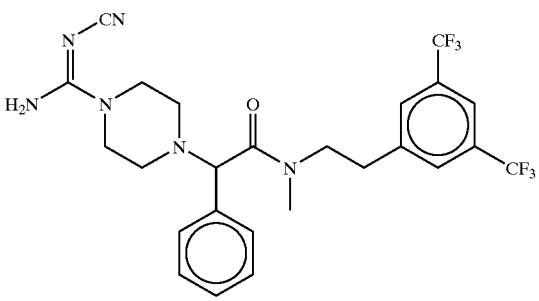

Example 17
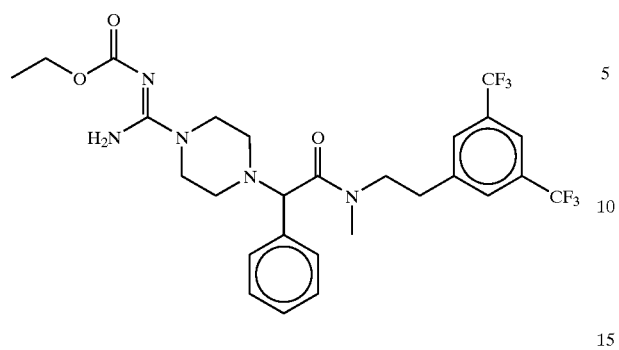
Example 21
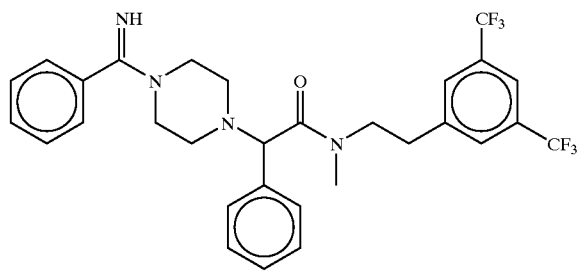
Example 18
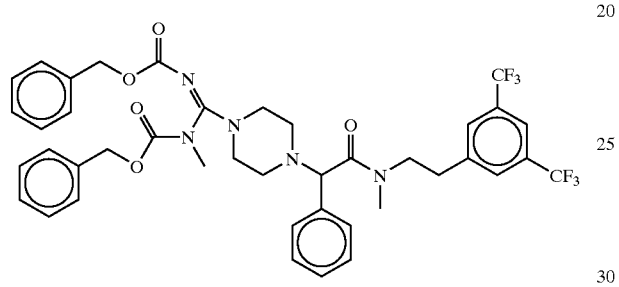
Example 22
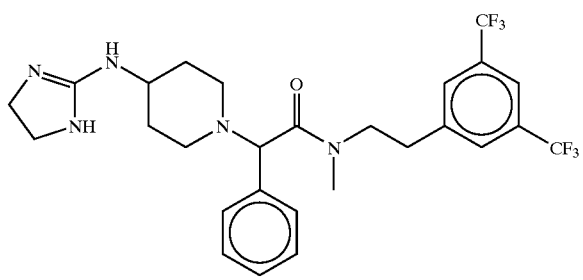
Example 19
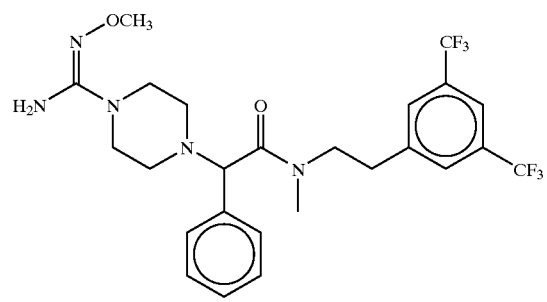
Example 23
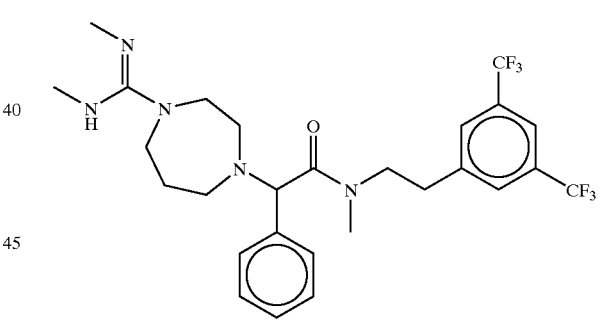
Example 20
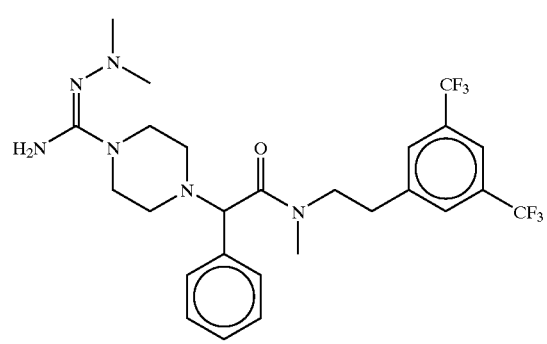
Example 25
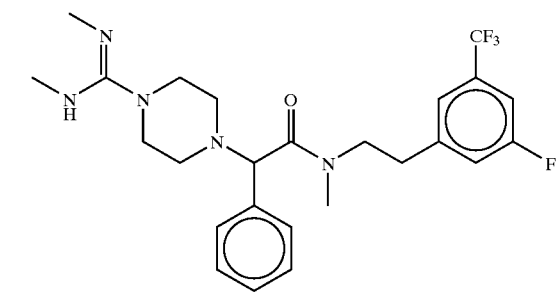

Example 26
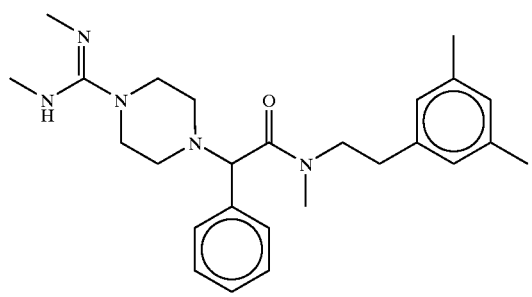
Example 27
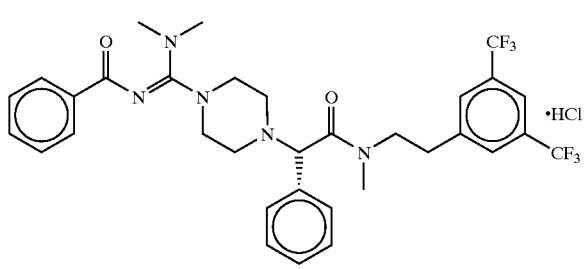
melting point: 124–128° C. FAB-MS: (M+H)⁺=648.2
Example 28
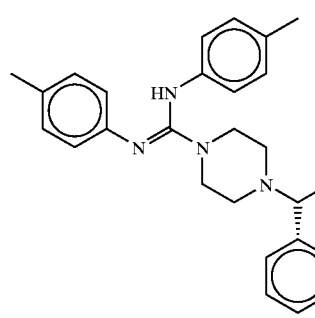
melting point: 193–1980 FAB-MS: (M+H)⁺=696.4
$[\alpha]_D^{20}$=+50.0° (DMSO)
Example 29
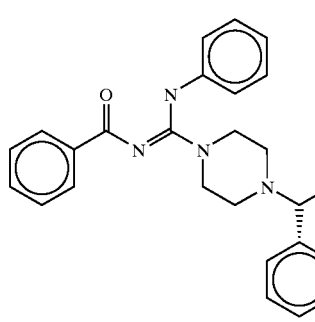
melting point: 146–149° $[\alpha]_D^{20}$=+48.8° (DMSO)
Example 30
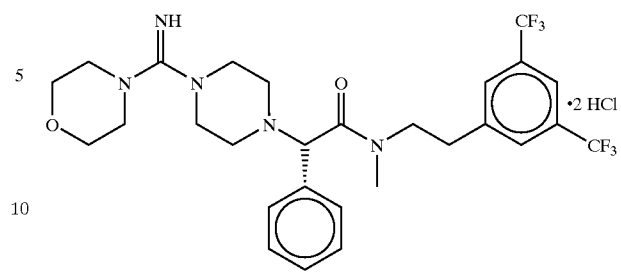
melting point: 90–100° $[\alpha]_D^{20}$=+23.6° (DMSO)
Example 31
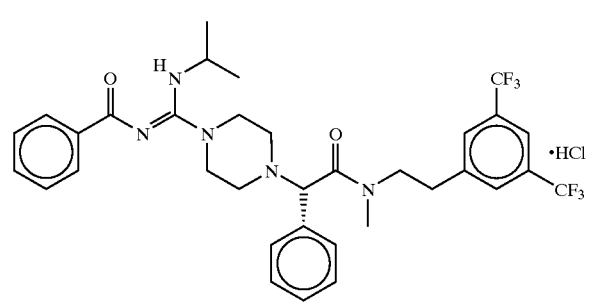
melting point: 170–180° FAB-MS: (M+H)⁺=661.9
Example 32
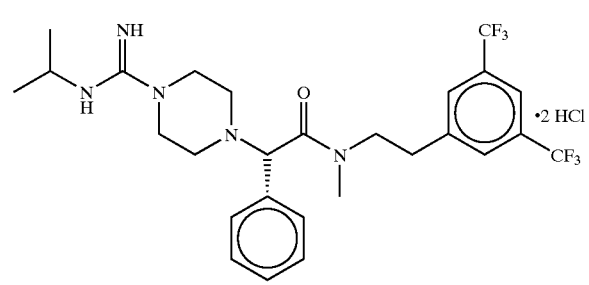
melting point: 84–94° $[\alpha]_D^{20}$=20.4° (DMSO)
Example 33
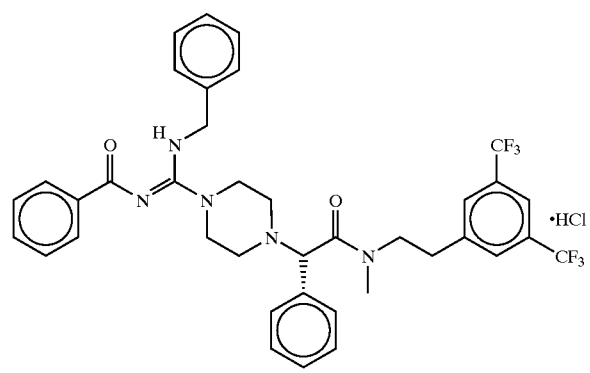
melting point: 169–179° $[\alpha]_D^{20}$=43.6° (DMSO)

Example 34

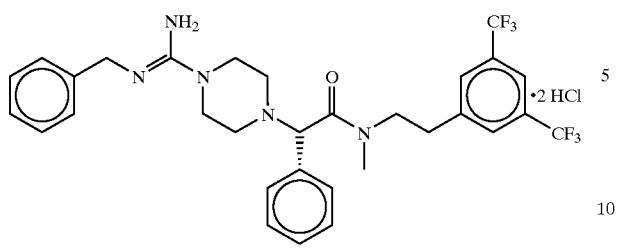

melting point: 131–141° $[\alpha]_D^{20}$=+25.2° (DMSO)

Example 35

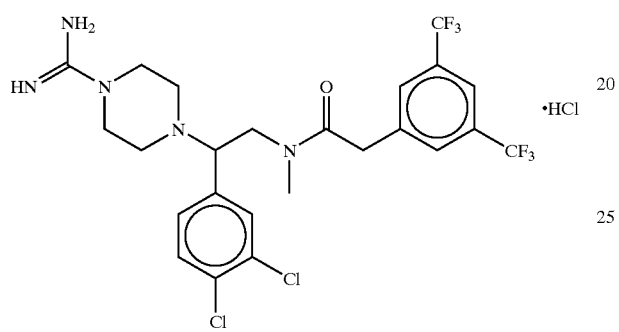

melting point:146–148° FAB-MS: (M+H)$^+$=584, 586, 588

Example 36

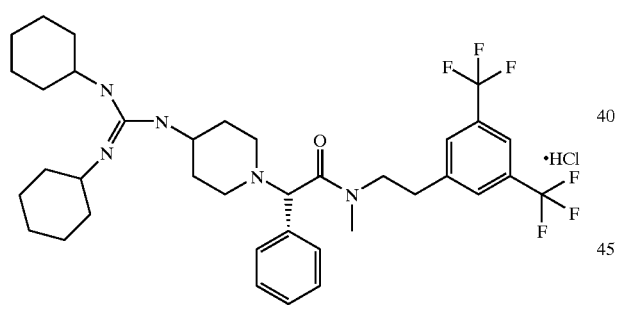

melting point: 126–134° C.

3.8 g of 4-amino-1-benzylpiperidine (20 mmol) was combined with 4.7 g of dicyclohexylcarbodiimide (23 mmol) in 80 ml of DMF and stirred for 12 hours at 80° C. The solvent was evaporated in vacuo and the residue was flash-chromatographed using ethyl acetate/methanol (1:1) whereby 54. g of 1-benzyl-4(N',N"-dicyclohexyl-guanidino)-piperidine was obtained (71%). 5 g of the product (12.6 mmol) was dissolved in 60 ml of methanol and hydrogenated using 0.6 g of Pd(C) at 2 bar hydrogen pressure. Thus obtained was 4 g of 4(N',N"-dicyclohexyl-guanidino)-piperidine (63%)

2.14 g of the product (7 mmol) was combined with 2.9 g of (R)-2-methylsulphonyloxy-N-methyl-N-[2-(3,5-bistrifluoromethyl-phenyl)-ethyl]-phenylacetamide (6 mmol), 60 ml of DMF and 0.96 ml of triethylamine and stirred for 3 hours at 65° C. The residue obtained after concentrating the raw product was chromatographed over silica gel with ethyl acetate/methanol (1:1) as an eluant, whereupon 0.6 g of the desired substance was obtained.

Example 37

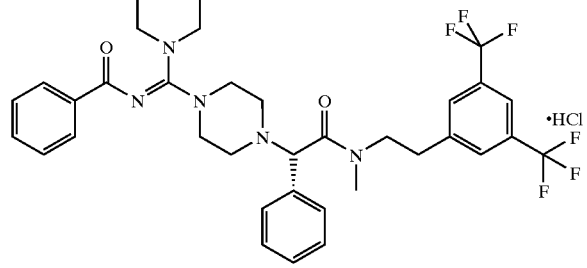

melting point: 114–124° C.

$[\alpha]20/D$=41.4° (DMSO).

Pharmaceutical Preparations

Injectable Solution 200 mg of active substance *

1.2 mg of monopotassium dihydrogen phosphate= KH$_2$PO$_4$)

0.2 mg of disodium hydrogen phosphate) (buffer)= NaH$_2$PO$_4$.2H$_2$O 94 mg of sodium chloride)(for an isotonic solution) or)

520 mg of glucose)

4 mg of albumin (protease protection)

q.s. sodium hydroxide solution)

q.s. hydrochloric acid ) ad pH 6 ad 10 ml water for injections

Injectable Solution 200 mg of active substance*

94 mg of sodium chloride or 520 mg of glucose 4 mg of albumin q.s. sodium hydroxide solution)

q.s. hydrochloric acid) ad pH 9 ad 10 ml water for injections

Lyophilisate 200 mg of active substance *

520 mg of mannitol (for isotonic solution/bulking agent)

4 mg of albumin solvent 1 for lyophilisate 10 ml water for injections solvent 2 for lyophilisate 20 mg Polysorbate®80=Tween®80 (surfactant)

10 ml water for injections

* active substance: compound according to the invention, e.g. one of Examples 1 to 35

Dosage for person weighing 67 kg: 1 to 500 mg

What is claimed is:

1. A process for the preparation of a compound of formula

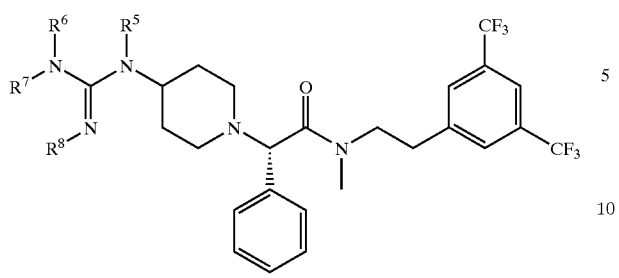

wherein
- $R^5$, $R^6$, $R^7$ independently of one another denote H, alkyl, cycloalkyl, alkenyl, aryl, aralkyl, alkanoyl, benzoyl, heteroaryl, dialkylamino, dialkylaminoalkyl, trialkylammoniumalkyl, cyano, alkyloxycarbonyl, aralkyloxycarbonyl, OH, O-alkyl or O-aryl, wherein the alkyl groups contain 1 to 5 carbon atoms, the cycloalkyl groups contain 3 to 6 carbon atoms, the alkenyl groups contain 2 to 5 carbon atoms,
- aryl denotes phenyl, or phenyl or naphthyl substituted by methyl or halogen; or
- $R^5$ and $R^6$ or $R^6$ and $R^7$ together form the group $(CH_2)_2-$, $-(CH_2)_3-$, $-(CH_2)_4-$, $-(CH_2)_5-$ or $-(CH_2)_2O(CH_2)_2$; and
- $R^8$ represents H, alkyl with 1 to 5 carbon atoms or cycloalkyl with 3 to 6 carbon atoms or
- $R^7+R^8$ together form the group $-(CH_2)_2-$, $-(CH_2)_3-$, $-(CH_2)_4-$, $-(CH_2)_5-$ or $-(CH_2)_2 O(CH_2)_2-$;

said process comprises reacting under suitable conditions an amide of formula

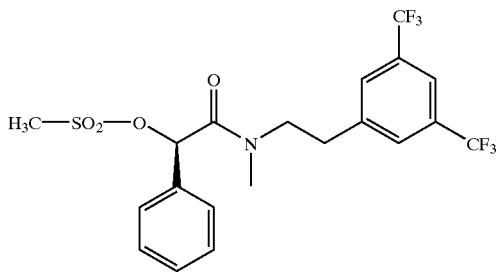

with a piperidine of formula

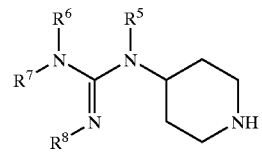

to produce the final product compound and if desired subsequently isolating the product; wherein
$R^5$, $R^6$, $R^7$ and $R^8$ have the meaning given above.

2. The process according to claim 1 wherein the reaction is carried out in an inert solvent in the presence of a base at temperatures between 20° C. and 120° C. and the reaction time is between 0.5 h and 48 h.

3. The process according to claim 2 wherein the inert solvent is chosen from DMF and acetonitrile and the base is chosen from TEA and N-methylmorpholine.

* * * * *